US009451998B2

(12) United States Patent
McBride et al.

(10) Patent No.: US 9,451,998 B2
(45) Date of Patent: Sep. 27, 2016

(54) SPINAL IMPLANT SYSTEM AND METHOD

(75) Inventors: Larry McBride, Memphis, TN (US); Nicholas Benson, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 466 days.

(21) Appl. No.: 13/588,765

(22) Filed: Aug. 17, 2012

(65) Prior Publication Data

US 2014/0052197 A1 Feb. 20, 2014

(51) Int. Cl.
*A61B 17/70* (2006.01)

(52) U.S. Cl.
CPC ......... *A61B 17/708* (2013.01); *A61B 17/7085* (2013.01)

(58) Field of Classification Search
CPC .......... A61B 17/7074; A61B 17/7076; A61B 17/7077; A61B 17/7079; A61B 17/708; A61B 17/7083; A61B 17/7085; A61B 17/7086; A61B 17/7088; A61B 17/7089; A61B 17/7091; A61B 17/7082
USPC ....... 606/246–279, 104, 86 A, 86 B, 99, 305
See application file for complete search history.

(56) References Cited

U.S. PATENT DOCUMENTS

| | | | |
|---|---|---|---|
| 3,963,028 A | 6/1976 | Cooley et al. | |
| 5,336,170 A | 8/1994 | Salerno | |
| 5,891,145 A | 4/1999 | Morrison et al. | |
| 6,228,022 B1 | 5/2001 | Friesem et al. | |
| 6,676,665 B2 | 1/2004 | Foley et al. | |
| 7,226,413 B2 | 6/2007 | McKinley | |
| 7,462,182 B2 * | 12/2008 | Lim | A61B 17/7086 606/99 |
| 7,476,240 B2 | 1/2009 | Raymond | |
| 7,491,218 B2 | 2/2009 | Landry et al. | |
| 7,563,264 B2 | 7/2009 | Landry et al. | |
| 7,575,581 B2 * | 8/2009 | Lovell | A61B 17/7076 606/104 |
| 7,597,694 B2 * | 10/2009 | Lim | A61B 17/7005 606/86 A |
| 7,666,189 B2 | 2/2010 | Gerber et al. | |
| 7,758,584 B2 * | 7/2010 | Bankoski | A61B 17/7076 606/104 |
| 7,794,464 B2 | 9/2010 | Bridwell et al. | |
| 7,802,574 B2 | 9/2010 | Schultz | |
| 7,842,044 B2 | 11/2010 | Runco et al. | |
| 7,846,093 B2 | 12/2010 | Gorek et al. | |
| 7,854,751 B2 | 12/2010 | Sicvol et al. | |
| 7,887,541 B2 | 2/2011 | Runco | |
| 7,914,558 B2 | 3/2011 | Landry et al. | |
| 7,918,857 B2 | 4/2011 | Dziedzic et al. | |
| 7,918,858 B2 | 4/2011 | Stad et al. | |
| 7,922,746 B2 | 4/2011 | Miller | |
| 7,927,334 B2 | 4/2011 | Miller | |
| 7,931,673 B2 * | 4/2011 | Hestad | A61B 17/7085 606/246 |
| 7,947,046 B2 * | 5/2011 | Justis | A61B 17/88 606/264 |

(Continued)

OTHER PUBLICATIONS

International Search Report and Written Opinion for PCT/US2013/050329, the counterpart application mailed on Oct. 10, 2013.

*Primary Examiner* — Lynnsy Summitt

(57) ABSTRACT

An extender comprises an inner member including a wall defining a thread form and at least one extension defining a first axial cavity and a second axial cavity, each cavity including first, second and third portions. An outer member includes an actuator and at least one arm having projections disposable with the portions of the axial cavities. The actuator is rotatable to axially translate the inner member such that the projections are disposable between a first position, a second position and a third position. Methods of use are disclosed.

20 Claims, 13 Drawing Sheets

(56) References Cited

U.S. PATENT DOCUMENTS

| | | | |
|---|---|---|---|
| 7,951,175 B2* | 5/2011 | Chao | A61B 17/8866 606/279 |
| 7,985,242 B2 | 7/2011 | Forton et al. | |
| 8,012,141 B2 | 9/2011 | Wright | |
| 8,096,996 B2 | 1/2012 | Gutierrez et al. | |
| 8,235,997 B2* | 8/2012 | Hoffman | A61B 17/7086 606/53 |
| 8,323,286 B2* | 12/2012 | Justis | A61B 17/708 606/264 |
| 8,439,922 B1* | 5/2013 | Arnold | A61B 17/7086 606/104 |
| 8,439,924 B1* | 5/2013 | McBride | A61B 17/708 606/104 |
| 8,460,300 B2* | 6/2013 | Hestad | A61B 17/7085 606/86 A |
| 8,545,505 B2* | 10/2013 | Sandstrom | A61B 17/7086 606/86 A |
| 8,617,218 B2* | 12/2013 | Justis | A61B 17/7076 606/278 |
| 8,709,044 B2* | 4/2014 | Chao | A61B 17/8866 606/246 |
| 2005/0070900 A1 | 3/2005 | Serhan et al. | |
| 2006/0074418 A1 | 4/2006 | Jackson | |
| 2006/0079903 A1 | 4/2006 | Wong | |
| 2006/0111712 A1 | 5/2006 | Jackson | |
| 2006/0111715 A1 | 5/2006 | Jackson | |
| 2006/0111730 A1 | 5/2006 | Hay | |
| 2006/0122597 A1 | 6/2006 | Jones | |
| 2006/0264962 A1 | 11/2006 | Chin et al. | |
| 2006/0293680 A1 | 12/2006 | Jackson | |
| 2007/0185375 A1 | 8/2007 | Stad et al. | |
| 2007/0213714 A1 | 9/2007 | Justis | |
| 2007/0244493 A1 | 10/2007 | Bjerken | |
| 2007/0270867 A1 | 11/2007 | Miller | |
| 2008/0015601 A1* | 1/2008 | Castro | A61B 17/7086 606/86 R |
| 2008/0172062 A1 | 7/2008 | Donahue | |
| 2008/0228233 A1* | 9/2008 | Hoffman | A61B 17/7088 606/86 A |
| 2008/0234678 A1 | 9/2008 | Gutierrez et al. | |
| 2008/0243190 A1 | 10/2008 | Dziedzic et al. | |
| 2009/0105771 A1 | 4/2009 | Lei | |
| 2009/0138055 A1 | 5/2009 | Altarac et al. | |
| 2009/0143828 A1 | 6/2009 | Stad et al. | |
| 2009/0157125 A1* | 6/2009 | Hoffman | A61B 17/7091 606/86 A |
| 2009/0171391 A1 | 7/2009 | Hutton | |
| 2009/0222046 A1 | 9/2009 | Gorek | |
| 2009/0228054 A1* | 9/2009 | Hoffman | A61B 17/7086 606/86 A |
| 2009/0228055 A1* | 9/2009 | Jackson | A61B 17/7086 606/86 A |
| 2009/0228056 A1 | 9/2009 | Jackson | |
| 2009/0234395 A1 | 9/2009 | Hoffman et al. | |
| 2009/0264895 A1 | 10/2009 | Gasperut | |
| 2009/0318972 A1 | 12/2009 | Jackson | |
| 2010/0030283 A1 | 2/2010 | King | |
| 2010/0036443 A1 | 2/2010 | Hutton | |
| 2010/0063552 A1 | 3/2010 | Chin et al. | |
| 2010/0069972 A1 | 3/2010 | Jones | |
| 2010/0198268 A1 | 8/2010 | Zhang et al. | |
| 2010/0198271 A1 | 8/2010 | Leone | |
| 2010/0312279 A1 | 12/2010 | Gephart et al. | |
| 2011/0015678 A1 | 1/2011 | Jackson | |
| 2011/0022088 A1 | 1/2011 | Jones | |
| 2011/0022093 A1* | 1/2011 | Sherman | A61B 17/7031 606/254 |
| 2011/0040335 A1* | 2/2011 | Stihl | A61B 17/7032 606/302 |
| 2011/0087298 A1* | 4/2011 | Jones | A61B 17/7086 606/86 A |
| 2011/0106178 A1 | 5/2011 | Schwab | |
| 2011/0202096 A1 | 8/2011 | White et al. | |
| 2011/0218581 A1* | 9/2011 | Justis | A61B 17/708 606/86 A |
| 2011/0264098 A1 | 10/2011 | Cobbs | |
| 2013/0018419 A1* | 1/2013 | Rezach | A61B 17/7076 606/264 |
| 2013/0041415 A1* | 2/2013 | Justis | A61B 17/708 606/86 A |
| 2013/0261679 A1* | 10/2013 | McBride | A61B 17/7085 606/86 A |
| 2014/0148865 A1* | 5/2014 | Hennard | A61B 17/7086 606/86 A |

* cited by examiner

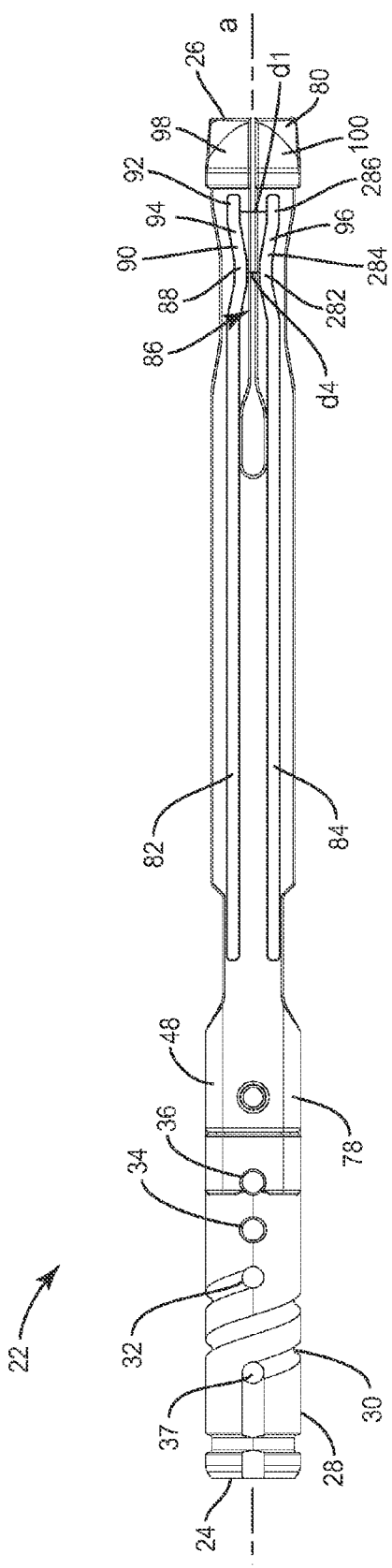
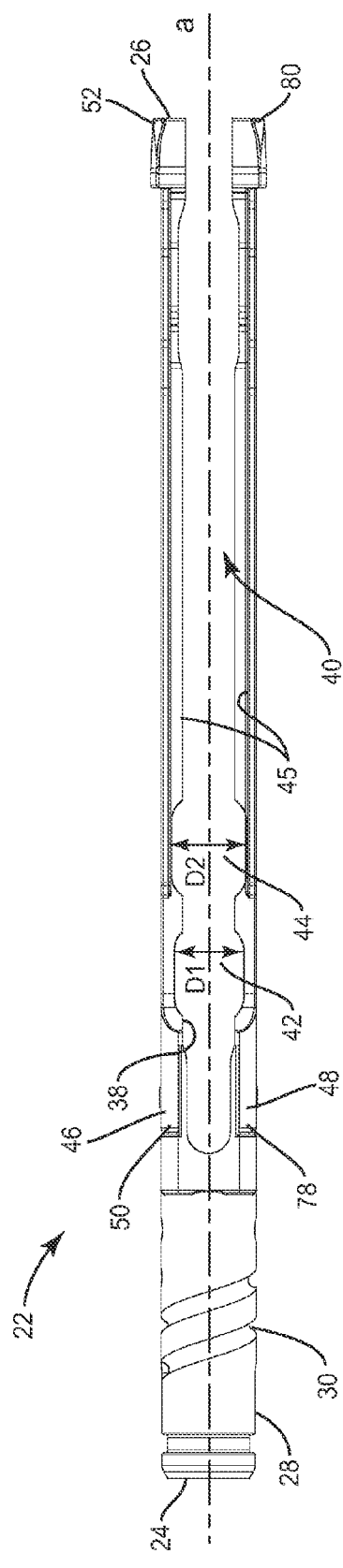
FIG. 3
FIG. 4

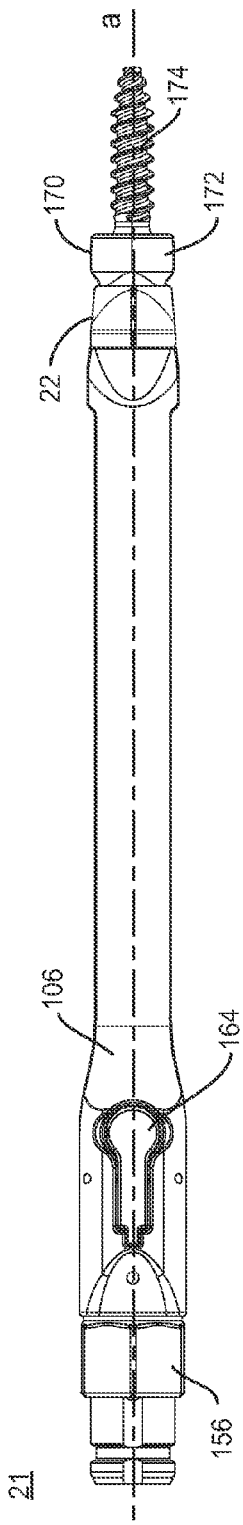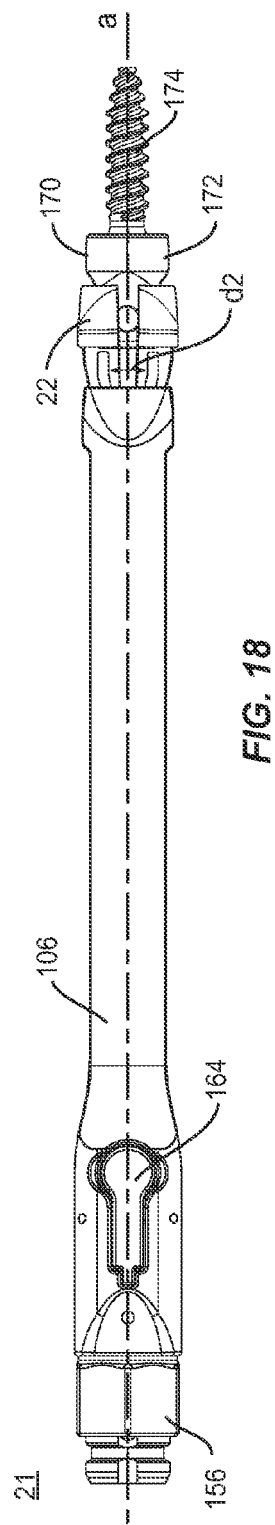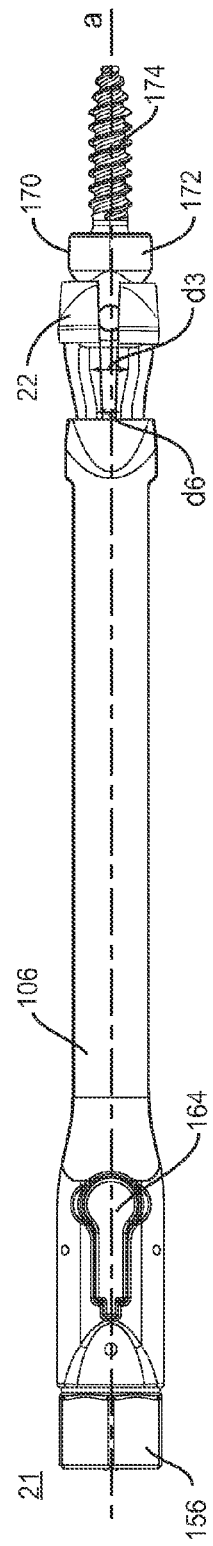

SPINAL IMPLANT SYSTEM AND METHOD

TECHNICAL FIELD

The present disclosure generally relates to medical devices for the treatment of musculoskeletal disorders, and more particularly to a surgical system for implant delivery to a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, in accordance with the principles of the present disclosure, an extender is provided. The extender comprises an inner member defining a longitudinal axis and including a wall defining a thread form. The inner member further includes at least one extension defining a first axial cavity and a second axial cavity. Each of the axial cavities includes a first portion, a second portion and a third portion. An outer member includes an actuator having a first part. The outer member further includes at least one arm having a first projection disposable with the portions of the first axial cavity and a second projection disposable with the portions of the second axial cavity. The actuator is rotatable so that the first part engages the thread form to axially translate the inner member relative to the outer member such that the projections are disposable between a first position such that the projections are disposed with the first portions of the respective axial cavity and the inner member is disposed in a non-expanded orientation, a second position such that projections are disposed with the second portions of the respective axial cavity and the inner member is disposed in an expanded orientation, and a third position such that the projections are disposed with the third portions of the respective axial cavity and the inner member is disposed in an expanded orientation.

In one embodiment, the extender comprises an inner sleeve extending between a proximal end and a distal end. The inner sleeve includes a longitudinal axis and a wall defining openings and a helical groove. The openings include a first lock opening, a second lock opening and a third lock opening. The inner sleeve further includes a first extension and a second extension. Each extension defines a first axial cavity and a second axial cavity. Each of the axial cavities include a first portion having a first dimension, a second portion having a second dimension and a third portion having a third dimension. The first dimension is greater than the second dimension and the second dimension is greater than the third dimension. Each portion is spaced apart and disposed in parallel relation. The distal end of each extension includes capture members that include at least one fixation portion. The inner sleeve further includes an inner surface that defines an implant cavity. The implant cavity extends between a first lateral opening and a second lateral opening. The lateral openings define a first dimension between the inner sleeve and a second dimension adjacent a proximal end thereof. The second dimension is greater than the first dimension. An outer sleeve includes an actuator comprising a knob having a gripping surface and including a first protuberance and a second protuberance. The outer sleeve further includes a first arm and a second arm. Each arm has at least one inward projection disposed for movement within each of the first axial cavities and second axial cavities. Each arm has flanges that define flange cavities configured for engagement with the distal end of the inner sleeve during axial translation of the inner member relative to the outer member. The knob is rotatable to a selected angular orientation such that the pins engage the thread form to axially translate the inner sleeve relative to the outer sleeve such that the projections are disposable between a first position such that the projections are disposed with the first portions of the respective axial cavity and the inner sleeve is disposed in a non-expanded orientation, a second position such that the projections are disposed with the second portions of the respective axial cavity and the inner sleeve is disposed in a first expanded orientation, and a third position such that the projections are disposed with the third portions of the respective axial cavity and the inner sleeve is disposed in a second expanded orientation.

In one embodiment, in accordance with the principles of the present disclosure, a spinal implant system is provided. The spinal implant system comprises an extender comprising an inner sleeve extending between a proximal end and a distal end and defining a longitudinal axis and an outer sleeve extending between a proximal end and a distal end. The inner sleeve includes a wall defining a thread form and lock openings. The lock openings include a first lock opening, a second lock opening and a third lock opening. The inner sleeve further includes a first extension and a second extension. Each extension defines a first axial cavity and a second axial cavity. Each of the axial cavities include a first portion having a first dimension, a second portion having a second dimension and a third portion having a third dimension. The first dimension is greater than the second dimension and the second dimension is greater than the third dimension. The distal ends of the extensions including a first capture member and a second capture member. Each capture member has at least one fixation portion. The outer sleeve includes an actuator including a first protuberance and a second protuberance. The outer sleeve further includes a first arm and a second arm. Each arm has a first inward projection disposed for movement within the first axial cavity and a second inward projection disposed for movement within the second axial cavity. The arms further include flanges that define flange cavities configured for disposal of the extensions such that the flanges slidably engage the extensions during axial translation. A bone fastener includes a proximal portion that defines an implant cavity and a distal portion configured to penetrate tissue. The actuator is rotated relative to the inner sleeve and the protuberances engage the thread form to the first lock opening such that the projections are disposed with the first portions of the respective axial cavity and the inner sleeve is disposed in a non-expanded locking orientation, the second lock opening such that the projections are disposed with the second portions of the respective axial cavity and the inner sleeve is disposed in a first expanded loading orientation, and the third lock opening such that the projections are disposed with the third portions of the respective axial cavity and the inner sleeve is disposed in a second expanded eject orientation.

BRIEF DESCRIPTION OF THE DRAWINGS

The present disclosure will become more readily apparent from the specific description accompanied by the following drawings, in which:

FIG. 3 is a side view of components of the system shown in FIG. 2;

FIG. 4 is a side view of components of the system shown in FIG. 2;

FIG. 17 is a side view of one embodiment of a system in accordance with the principles of the present disclosure;

FIG. 18 is a side view of the system shown in FIG. 17;

FIG. 19 is a side view of the system shown in FIG. 17; and

Like reference numerals indicate similar parts throughout the figures.

DETAILED DESCRIPTION

Figure 1:
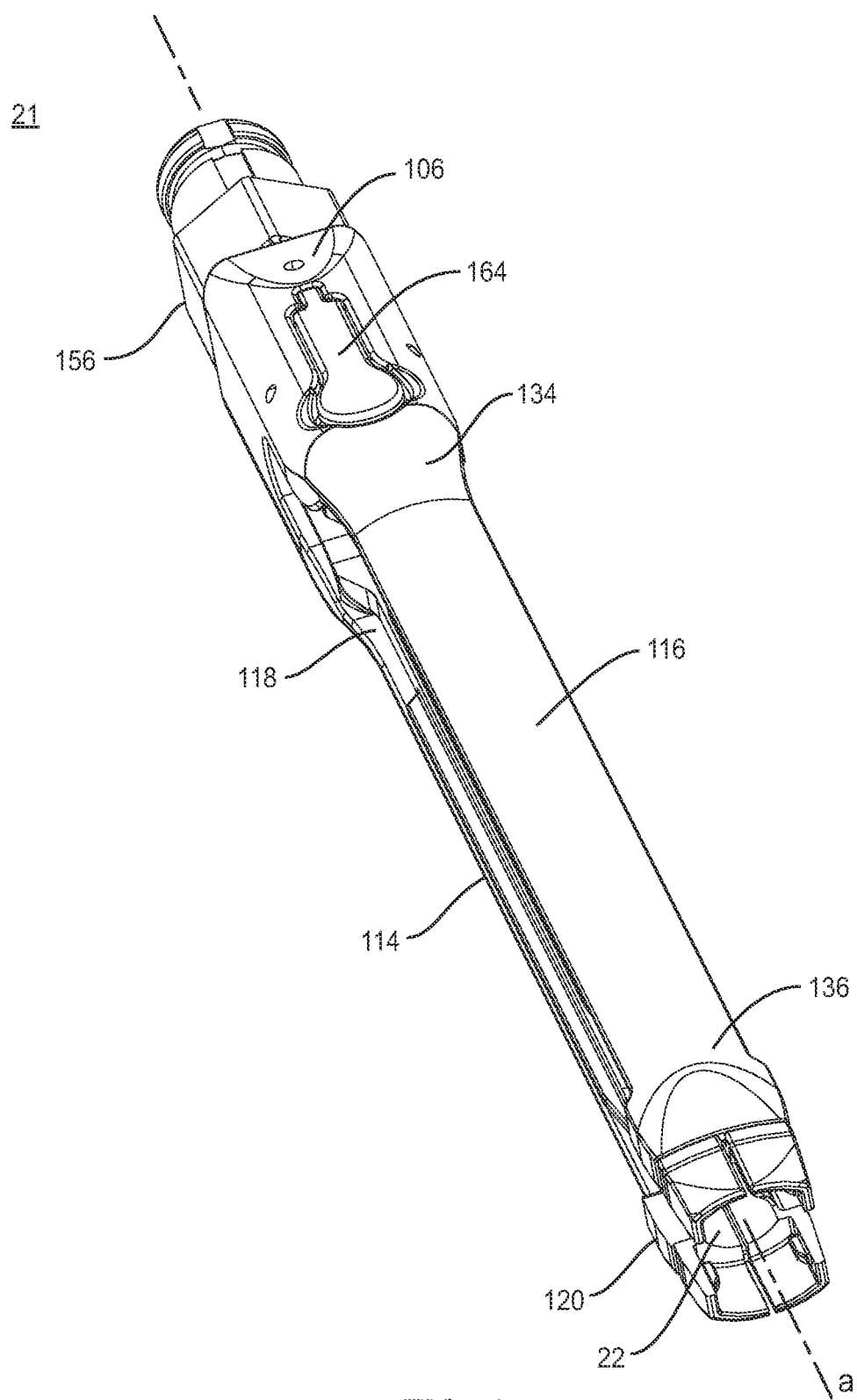
FIG. 1 is a perspective view of one particular embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system for implant delivery to a surgical site and a method for treating a spine. In one embodiment, the surgical implant system can include a bone fastener that allows capture and retention under tension and compression. It is envisioned that compression may be applied in a cephalad/caudal direction or a lateral direction. It is further envisioned that the tension may be applied through a member, such as, for example, an extender and that compression may be applied through another member, such as, for example, a sleeve. In one embodiment, the surgical system of the present disclosure includes an extender that employs a rotating knob to drive the axial movement of its component parts to a lock, load and/or an eject position to capture an implant such as a head of a multi-axial screw (MAS).

It is envisioned that the system may include instruments that are connected or attached to an extender(s) such as, for example, a lateral translation handle or derotaton instruments. It is further envisioned that the system may have an extender with a quick release mechanism to allow the extender to slide into engagement with an implant. It is contemplated that the system can include an extender having features that prevent an implant from rotating. In one embodiment, one or all of the components of the surgical system are disposable, peel-pack, pre-packed sterile devices used with an implant. One or all of the components of the surgical system may be reusable. The surgical system may be configured as a kit with multiple sized and configured components.

In one embodiment, the surgical system of the present disclosure includes one or a plurality of openings defined in an inner assembly that engage an actuator of an outer assembly. For example, a first opening provides inspection, a second opening provides inspection and a lock for an eject position, a third opening provides a load position and a fourth opening provides a locked position. In one embodiment, the inner assembly includes a custom thread that facilitates axial translation of the component parts. In one embodiment, the inner assembly includes areas of removed material to allow pins of the outer assembly to move within these areas to load and unload a bone fastener, such as, a MAS. In one embodiment, the inner assembly is comprised of three components that are welded together to prevent undesired bending of extensions of the inner assembly during manufacturing. In one embodiment, the outer assembly includes a distal end having a wrap-around configuration to hold the inner assembly.

In one embodiment, the surgical system of the present disclosure includes angular cuts in the outer assembly to allow for clearance for mating with surgical instruments, such as a rod reducer. It is contemplated that the inner assembly and the outer assembly are tapered to create a smooth transition from an implant to the assemblies. In one embodiment, the inner assembly includes at least one radial groove to allow for attachment with a surgical instrument to facilitate rod reduction. In one embodiment, the outer assembly includes cuts to increase opening or window dimension for the passage of implants, such as a spinal rod therethrough, for example adjacent a proximal end of the assemblies. In one embodiment, the inner assembly includes cuts that facilitate passage of a spinal rod through a window adjacent the cuts and prevents passage of the rod through the window adjacent other portions of the inner assembly. It is contemplated that the inner assembly and/or the outer assembly may include one or a plurality of openings or windows that include portions that facilitate passage of implants therethrough and portions that prevent passage of portions and/or assemblies of the implants therethrough.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed surgical system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference will now be made in detail to the exemplary embodiments of the present disclosure, which are illustrated in the accompanying figures. Turning now to FIGS. 1-19, there is illustrated components of a surgical system, such as, for example, a spinal implant system 21 in accordance with the principles of the present disclosure.

The components of spinal implant system 21 can be fabricated from biologically acceptable materials suitable for medical applications, including metals, synthetic polymers, ceramics and bone material and/or their composites, depending on the particular application and/or preference of a medical practitioner. For example, the components of spinal implant system 21, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of spinal implant system 21 may have material composites, including the above materials, to achieve various desired characteristics such as strength, rigidity, elasticity, compliance, biomechanical performance, durability and radiolucency or imaging preference. The components of spinal implant system 21, individually or collectively, may also be fabricated from a heterogeneous material such as a combination of two or more of the above-described materials. The components of spinal implant system 21 may be monolithically formed, integrally connected or include fastening elements and/or instruments, as described herein.

Spinal implant system 21 is employed, for example, with a minimally invasive procedure, including percutaneous techniques, mini-open and open surgical techniques to deliver and introduce an implant, such as, for example, a bone fastener, at a surgical site within a body of a patient, for example, a section of a spine. It is contemplated that the spinal implant system and method may be employed with treatments using minimally invasive and percutaneous techniques.

Figure 2:
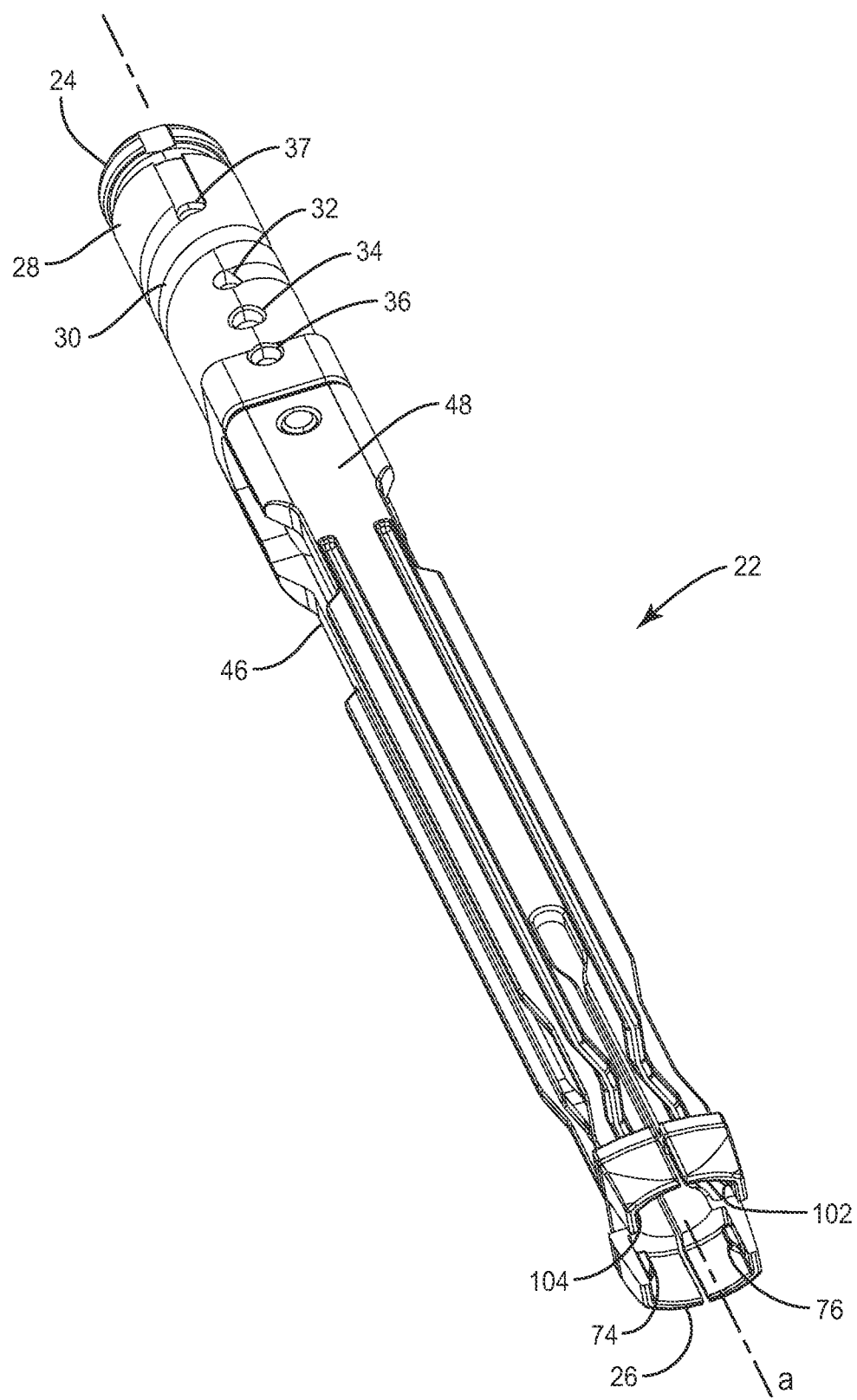
FIG. 2 is a perspective view of components of the system shown in FIG. 1.
Figure 5:
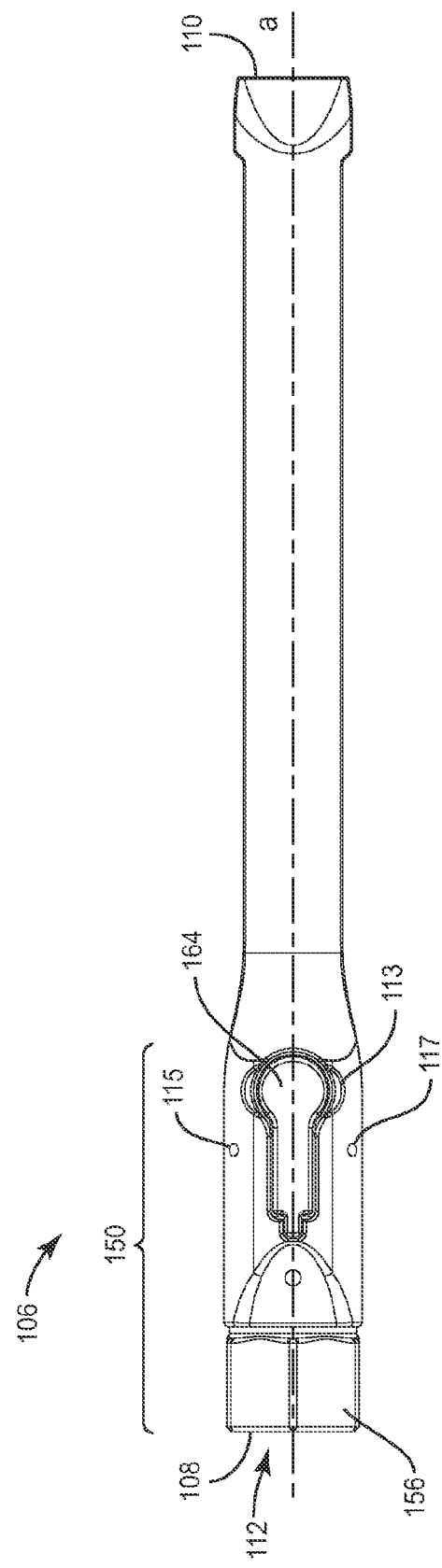
FIG. 5 is a side view of components of the system shown in FIG. 1.
Figure 6:
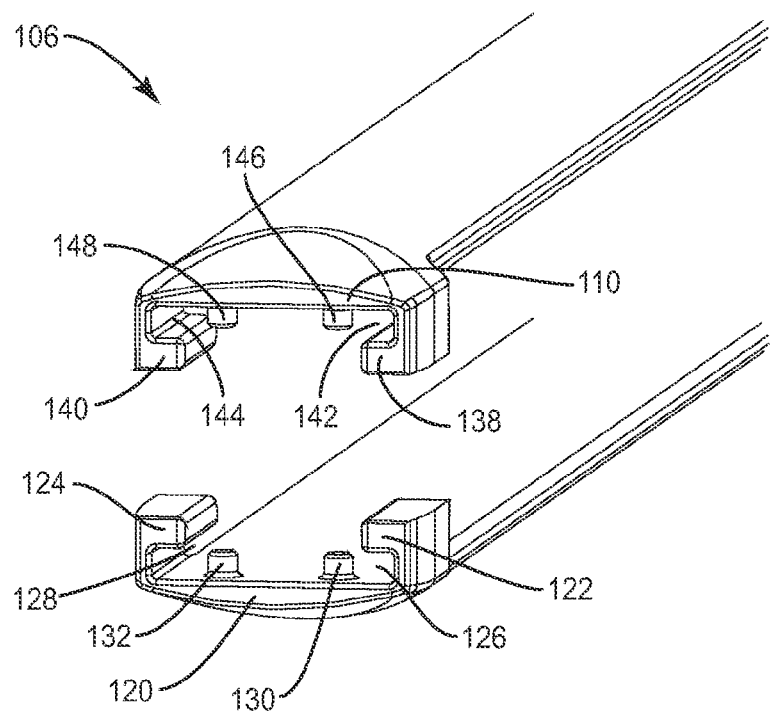
FIG. 6 is a break away end view of a component of the system shown in FIG. 1.
Figure 7:
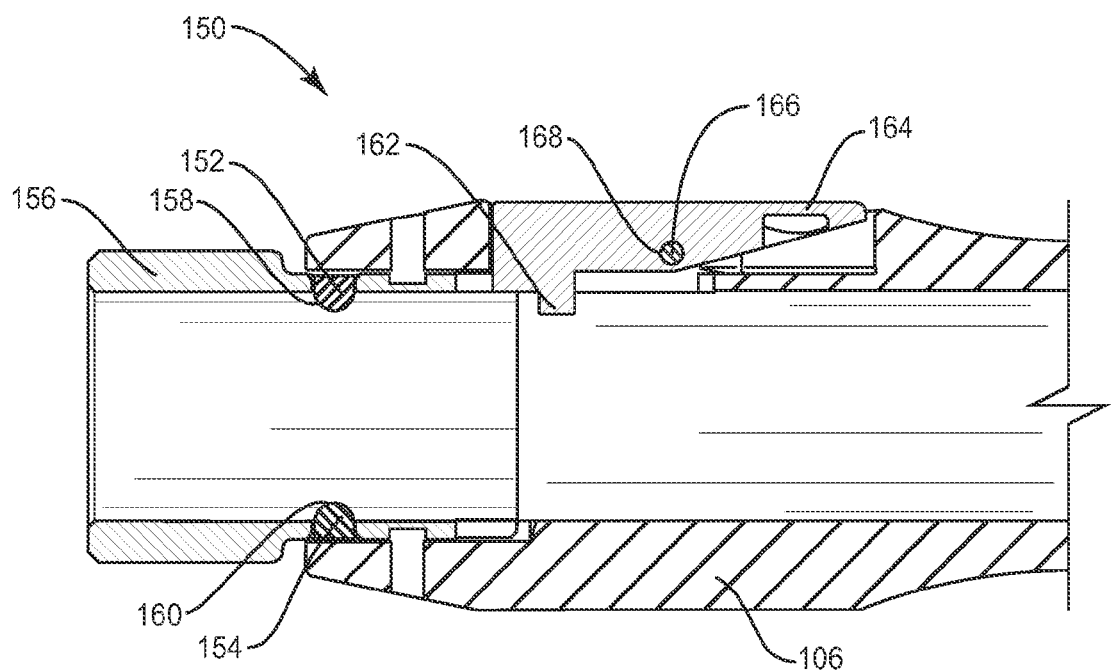
FIG. 7 is a break away cross section view of components of the system shown in FIG. 1.

Spinal implant system 21 includes a first member, such as, for example, an inner sleeve 22, as shown in FIGS. 2-4. Inner sleeve 22 extends between a proximal end 24 and a distal end 26. Inner sleeve 22 defines a first longitudinal axis a. It is contemplated that the cross-section of inner sleeve 22 may have various configurations, for example, round, cylindrical, partially cylindrical, oval, rectangular, polygonal, irregular, tapered, offset, staggered, uniform and non-uniform. It is further envisioned that one or all of the surfaces of inner sleeve 22 may have alternate surface configurations, such as, for example, rough, threaded for connection with surgical instruments, arcuate, undulating, porous, semi-porous, dimpled, polished and/or textured according to the requirements of a particular application.

Proximal end 24 includes an outer wall 28. Wall 28 defines a thread form, such as, for example, helical groove 30. Groove 30 is configured for engagement with an outer sleeve, as described herein. Wall 28 includes openings, such as, for example, a first lock opening 32 that communicates with groove 30, a second lock opening 34 spaced apart from opening 32 and a third lock opening 36 spaced apart from opening 34. In one embodiment, opening 32 is spaced apart from and not in communication with groove 30. Wall includes an opening 37 that communicates with groove 30 and provides visual inspection of an interior cavity of inner sleeve 22. In one embodiment, opening 37 is spaced apart from and not in communication with groove 30. It is contemplated that the openings may have various configurations, for example, round, oval, rectangular, polygonal, irregular, offset, staggered, uniform and non-uniform. Openings 32, 34 and 36 are configured for engagement with a portion of an outer sleeve, as described herein. In one embodiment, wall 28 includes groove 30 and no lock openings such that the outer sleeve is freely engageable with groove 30.

Inner sleeve 22 includes an inner surface 38 that defines an implant cavity 40. Cavity 40 extends axially along inner sleeve 22 between ends 24, 26. It is contemplated that the cross-section of cavity 40 may have various configurations, for example, round, oval, rectangular, polygonal, irregular, tapered, offset, staggered and uniform. Cavity 40 is configured for disposal of an implant and/or an implant assembly, such as, for example, a vertebral rod construct.

In one embodiment, as shown in FIG. 4, cavity 40 extends laterally between lateral openings 42 disposed on opposing sides of sleeve 22 adjacent proximal end 24. Lateral openings 42 each define a dimension, such as, for example, a diameter D1. Cavity 40 also extends laterally between lateral openings 44 disposed on opposing sides of sleeve 22. Lateral openings 44 each define a dimension, such as, for example, a diameter D2. D2 has a greater dimension than D1 to provide alternate window sizes for passage of alternately sized implants or portions of implants. Lateral openings 42 and openings 44 increase window dimension for the passage of implants, such as a spinal rod therethrough. The configuration of openings 42 and openings 44 facilitate passage of a spinal rod through a window. Inner sleeve 22 includes wall surfaces 45 that prevent passage of a portion of a spinal rod, which has portions of varying size and shape, through the window provided by inner sleeve 22. It is contemplated that inner sleeve 22 may include one or a plurality of openings or windows that include portions that facilitate passage of implants therethrough and portions that prevent passage of portions and/or assemblies of implants therethrough. It is contemplated that D1 may have a greater dimension than D1, or equal dimensions.

Figure 14:
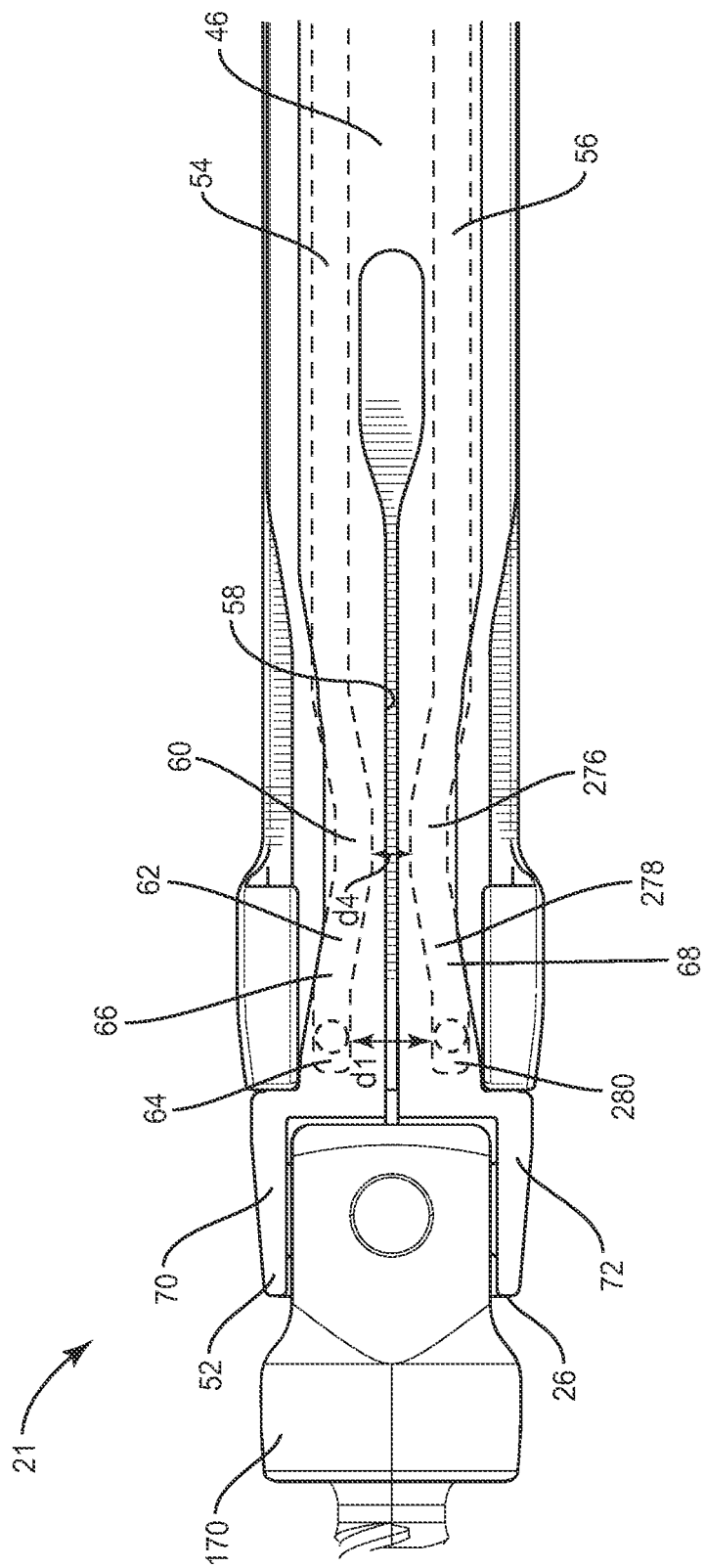
FIG. 14 is a break away cross section view of components of the system shown in FIG. 1.

Inner sleeve 22 includes two spaced apart extensions 46, 48. Extension 46 extends between a proximal end 50 and a distal end 52. Extension 46 includes a first sliding contact surface, which includes a surface 54 and a surface 56, as shown in FIG. 14. Surfaces 54, 56 have a smooth and even configuration for movable engagement with a surface of an outer sleeve, discussed below. It is envisioned that surfaces 54, 56 may have various surface configurations, such as those alternatives described herein.

Figure 15:
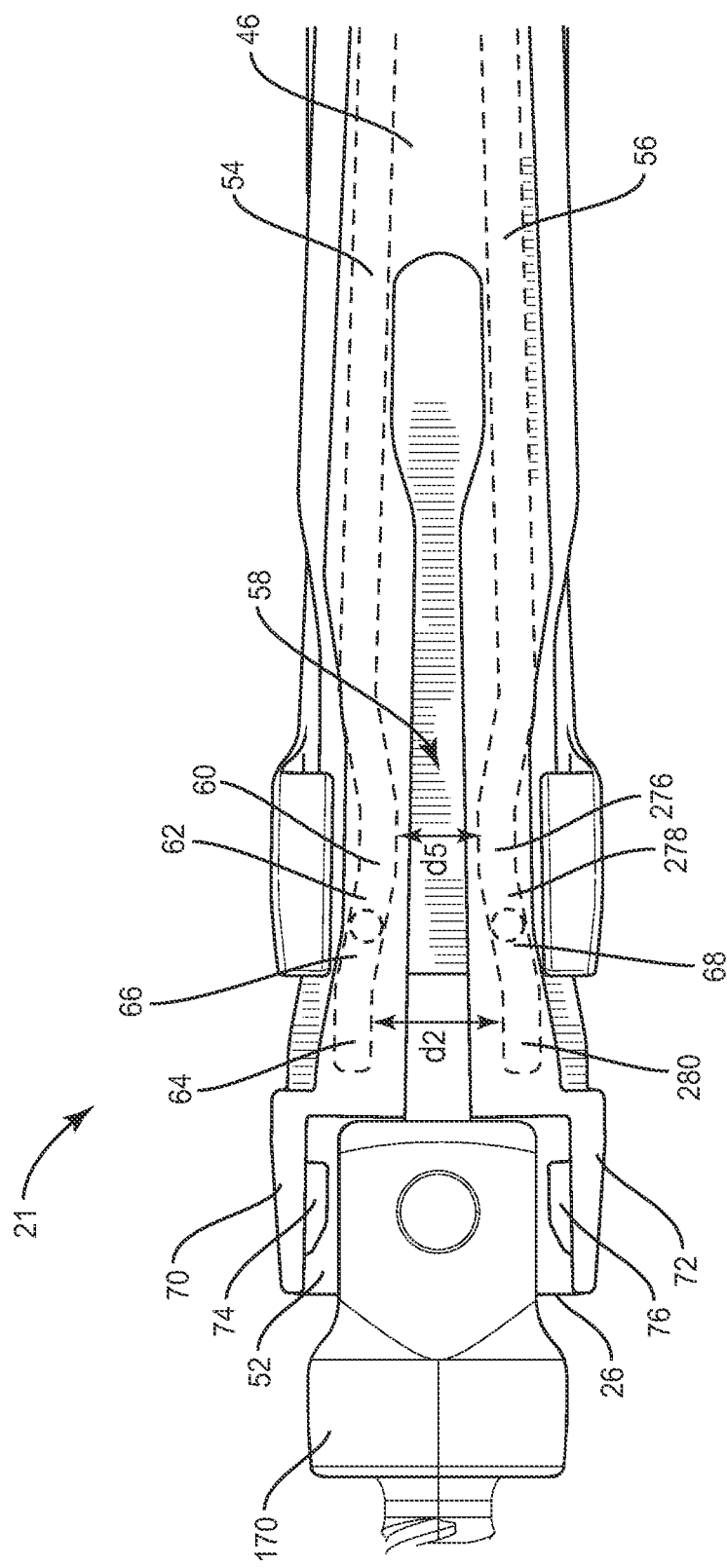
FIG. 15 is a break away cross section view of components of the system shown in FIG. 1.
Figure 16:
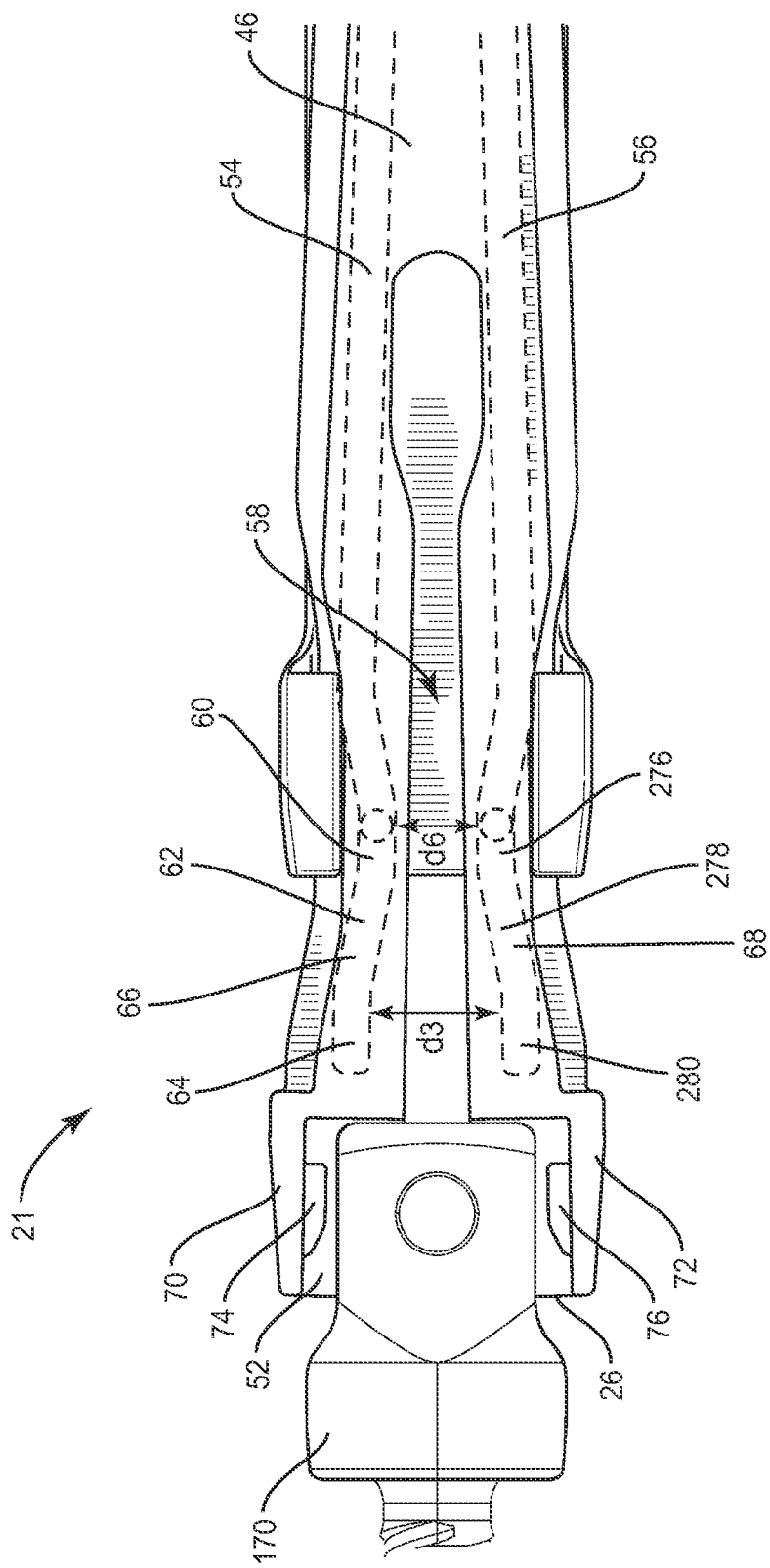
FIG. 16 is a break away cross section view of components of the system shown in FIG. 1.

Surfaces 54, 56 are spaced apart about an expandable axial cavity, such as, for example, axial slot 58 that is disposed adjacent distal end 52. Slot 58 expands and contracts due to axial translation of the component parts of system 21. Surface 54 includes a first portion, such as, for example, a proximal portion 60, a second portion, such as, for example, an intermediate portion 62 and a third portion, such as, for example, a distal portion 64, as shown in FIGS. 14-16. Surface 56 includes a first portion, such as, for example, a proximal portion 276, a second portion, such as, for example, an intermediate portion 278 and a third portion, such as, for example, a distal portion 280, as shown in FIGS. 14-16. Surfaces 54, 56 are configured for slidable engagement with pins and an outer sleeve, as described herein.

Surfaces 54, 56 are spaced apart a distance d1 adjacent distal portions 64, 280 in a non-expanded orientation of inner sleeve 22. Inner sleeve 22 is expandable to a first expanded orientation, as shown in FIG. 15, such that surfaces 54, 56 are spaced apart a distance d2 adjacent distal portions 64, 280. Inner sleeve 22 is expandable to a second expanded orientation, as shown in FIG. 16, such that surfaces 54, 56 are spaced apart a distance d3 adjacent distal portions 64, 280. As such, slot 58 can be expanded and contracted adjacent distal portions 64, 280 within a range of expansion between distance d1, distance d2 and distance d3. Distance d3 has a dimension greater than distance d2 and distance d2 has a dimension greater than distance d1.

Intermediate portions 62, 278 of surfaces 54, 56 are disposed between portions 60, 64 and 276, 280 respectively. Surface 54 defines a first ramp 66, which defines intermediate portion 62. Ramp 66 extends between a proximal end and a distal end, which define an inclination therebetween that facilitates expansion of inner sleeve 22 between the non-expanded orientation and the expanded orientation. Surface 56 defines a second ramp 68, which defines intermediate portion 278. Ramp 68 extends between a proximal end and a distal end, which define an inclination therebetween that facilitates expansion of inner sleeve 22 between the non-expanded orientation and the expanded orientation. Portions 60, 62, 64 and 276, 278, 280 are each spaced apart and disposed in parallel relation to one another.

Surfaces 54, 56 are spaced apart a distance d4 adjacent proximal portions 60, 276 in the non-expanded orientation of inner sleeve 22, as shown in FIG. 14. Inner sleeve 22 is expandable to the first expanded orientation, as shown in FIG. 15, such that surfaces 54, 56 are spaced apart a distance d5 adjacent proximal portions 60, 276. Inner sleeve 22 is expandable to the second expanded orientation, as shown in FIG. 16, such that surfaces 54, 56 are spaced apart a distance d6 adjacent proximal portions 60, 276. As such, slot 58 can be expanded and contracted adjacent proximal portions 60, 276 within a range of expansion between distance d4, distance d5 and distance d6. Distance d6 has a dimension greater than distance d5 and distance d5 has a dimension greater than distance d4.

In one embodiment, d1 is greater than d4. In one embodiment, d2 is greater than d5. In one embodiment, d3 is greater than d6.

Extension 46 includes a capture member 70 and a capture member 72, disposed adjacent distal end 26. Members 70, 72 both include an inner surface that defines an implant cavity configured for disposal of at least a portion of an implant, such as, for example, a bone fastener. The inner surfaces of members 70, 72 include at least one fixation surface, such as, for example, projection 74 and projection 76 respectively, that extends into the implant cavities of members 70, 72 to engage the bone fastener for retaining the bone fastener with inner sleeve 22. The inner surface includes a planar face and an arcuate face. It is contemplated that all or only a portion of the inner surface may have alternate surface configurations to enhance fixation with the bone fastener, such as, for example, dimpled and/or textured. It is contemplated that the projection may include a nail configuration, raised elements and/or spikes to facilitate engagement of the members with the bone fastener.

Members 70, 72 extend from distal end 52 of extension 46 such that members 70, 72 are biased for engagement. Members 70, 72 are movable between a non-expanded orientation (FIG. 14) and an expanded orientation (FIGS. 15-16). In the non-expanded orientation, the surfaces of members 70, 72 are disposed in a flush contacting engagement such that, for example, members 70, 72 capture and/or retain the bone fastener. Projections 74, 76 engage the bone fastener to releasably lock the bone fastener with members 70, 72. Members 70, 72 are expandable and separable, via engagement with the outer sleeve as described herein, to dispose members 70, 72 in the expanded orientation. In the expanded orientation, members 70, 72 are spaced apart such that, for example, members 70, 72 release and/or eject the bone fastener from members 70, 72. Projections 74, 76 disengage from the bone fastener.

Extension 48 extends between a proximal end 78 and a distal end 80. Extension 48 includes a first sliding contact surface, which includes a surface 82 and a surface 84. Surfaces 82, 84 have a smooth and even configuration for movable engagement with a surface of an outer sleeve, discussed below. It is envisioned that surfaces 82, 84 may have various surface configurations, such as those alternatives described herein.

Surfaces 82, 84 are spaced apart about an expandable axial cavity, such as, for example, axial slot 86 that is disposed adjacent distal end 80. Slot 86 expands and contracts due to axial translation of the component parts of system 21. Surface 82 includes a first portion, such as, for example, a proximal portion 88, a second portion, such as, for example, an intermediate portion 90 and a third portion, such as, for example, a distal portion 92, as shown in FIG. 3. Surface 84 includes a first portion, such as, for example, a proximal portion 282, a second portion, such as, for example, an intermediate portion 284 and a third portion, such as, for example, a distal portion 286, as shown in FIG. 3. Surfaces 82, 84 are configured for slidable engagement with pins and an outer sleeve, as described herein Surfaces 82, 84 are spaced apart a distance d1 adjacent distal portions 92, 286 in a non-expanded orientation of inner sleeve 22. Inner sleeve 22 is expandable to a first expanded orientation, as shown in FIG. 18, such that surfaces 82, 84 are spaced apart a distance d2 adjacent distal portions 92, 286. Inner sleeve 22 is expandable to a second expanded orientation, as shown in FIG. 19, such that surfaces 54, 56 are spaced apart a distance d3 adjacent distal portions 92, 286. As such, slot 86 can be expanded and contracted adjacent distal portions 92, 286 within a range of expansion between distance d1, distance d2 and distance d3. Distance d3 has a dimension greater than distance d2 and distance d2 has a dimension greater than distance d1.

Intermediate portions 90, 284 of surfaces 82, 84 are disposed between portions 88, 92 and 282, 286 respectively. Surface 82 defines a first ramp 94, which defines intermediate portion 90. Ramp 94 extends between a proximal end and a distal end, which define an inclination therebetween that facilitates expansion of inner sleeve 22 between the non-expanded orientation and the expanded orientation. Surface 84 defines a second ramp 96, which defines intermediate portion 284. Ramp 96 extends between a proximal end and a distal end, which define an inclination therebetween that facilitates expansion of inner sleeve 22 between the non-expanded orientation and the expanded orientation. Portions 88, 90, 92 and 282, 284, 286 are each spaced apart and disposed in parallel relation to one another.

Surfaces 82, 84 are spaced apart a distance d4 adjacent proximal portions 88, 282 in the non-expanded orientation of inner sleeve 22, as shown in FIG. 3. Inner sleeve 22 is expandable to the first expanded orientation, as shown in FIG. 18, such that surfaces 82, 84 are spaced apart a distance d5 (similar to distance d5 in FIG. 15) adjacent proximal portions 88, 282. Inner sleeve 22 is expandable to the second expanded orientation, as shown in FIG. 19, such that surfaces 82, 84 are spaced apart a distance d6 adjacent proximal portions 88, 282. As such, slot 86 can be expanded and contracted adjacent proximal portions 88 within a range of expansion between distance d4, distance d5 and distance d6. Distance d6 has a dimension greater than distance d5 and distance d5 has a dimension greater than distance d4.

In one embodiment, d1 is greater than d4. In one embodiment, d2 is greater than d5. In one embodiment, d3 is greater than d6.

Extension 48 includes a capture member 98 and a capture member 100, disposed adjacent distal end 80. Members 98, 100 both include an inner surface that defines an implant cavity configured for disposal of at least a portion of an implant, such as, for example, a bone fastener. The inner surfaces of members 98, 100 include at least one fixation surface, such as, for example, projection 102 and projection 104 respectively, that extends into the implant cavities of members 98, 100 to engage the bone fastener for retaining the bone fastener with inner sleeve 22. The inner surface includes a planar face and an arcuate face. It is contemplated that all or only a portion of the inner surface may have alternate surface configurations to enhance fixation with the bone fastener, such as, for example, dimpled and/or textured. It is contemplated that the projection may include a nail configuration, raised elements and/or spikes to facilitate engagement of the members with the bone fastener.

Members 98, 100 extend from distal end 80 of extension 48 such that members 98, 100 are biased for engagement. Members 98, 100 are movable between a non-expanded orientation (FIG. 17) and an expanded orientation (FIGS. 18-19). In the non-expanded orientation, the surfaces of members 98, 100 are disposed in a flush contacting engagement such that, for example, members 98, 100 capture and/or retain the bone fastener. Projections 102, 104 engage the bone fastener to releasably lock the bone fastener with members 98, 100. Members 98, 100 are expandable and separable, via engagement with the outer sleeve as described herein, to dispose members 98, 100 in the expanded orientation. In the expanded orientation, members 98, 100 are spaced apart such that, for example, members 98, 100 release and/or eject the bone fastener from members 98, 100. Projections 102, 104 disengage from the bone fastener.

A second member, such as, for example, an outer sleeve 106 is configured for slidable engagement with inner sleeve 22. Outer sleeve 106 extends between a proximal end 108 and a distal end 110. Outer sleeve 106 extends along longitudinal axis a and is mounted with inner sleeve 22 for axial translation relative to inner sleeve 22. It is contemplated that the cross-section of outer sleeve 106 may have various configurations, for example, round, oval, rectangular, polygonal, irregular, tapered, offset, staggered, uniform and non-uniform. It is further envisioned that one or all of the surfaces of outer sleeve 106 may have alternate surface configurations, such as, for example, rough, threaded for connection with surgical instruments, arcuate, undulating, porous, semi-porous, dimpled, polished and/or textured according to the requirements of a particular application.

Outer sleeve 106 includes a cavity, such as, for example, channel 112 that extends through outer sleeve 106. Channel 112 has a cylindrical cross-section configuration. It is contemplated that the cross-section of channel 112 may have various configurations, for example, round, oval, rectangular, polygonal, irregular, tapered, offset, staggered, uniform and non-uniform. Channel 112 is configured for disposal of inner sleeve 22, as described herein. Outer sleeve 106 includes a recess 113. Recess 113 is configured for engagement with a biasing member, as described herein. Outer sleeve 106 includes openings 115 and 117. Openings 115, 117 are configured for engagement with a biasing member, as described herein.

Outer sleeve 106 includes two spaced apart arms 114 and 116. Arm 114 extends between a proximal end 118 and a distal end 120. Arm 114 includes flanges 122, 124. Flanges 122, 124 are disposed at distal end 120. Flange 122 defines a flange cavity 126 and flange 124 defines a flange cavity 128. Cavities 126, 128 are configured for disposal of inner sleeve 22 such that flanges 122, 124 wrap around and slidably engage inner sleeve 22 during, for example, axial translation of the components of system 21.

Arm 114 includes projections, such as, for example, pin 130 and pin 132. Pins 130, 132 are configured for engagement with surfaces 54, 56 that are spaced apart about axial slot 58. Pins 130, 132 extend in a transverse orientation relative to a longitudinal axis within surfaces 54, 56. Pins 130, 132 engage surfaces 54, 56 such that members 70, 72 are movable between the non-expanded orientation and the expanded orientation, as described herein. It is envisioned that pins 130, 132 can be variously configured with regard to size and shape, and the shape may be rectangular, triangular, polygonal, and hexagonal, for example. It is further envisioned that the sliding contact surface may comprise a hook, clip, rod, tab, detent and/or key/keyway for slidable engagement with inner sleeve 22.

Arm 116 extends between a proximal end 134 and a distal end 136. Arm 116 includes flanges 138, 140. Flanges 138, 140 are disposed at distal end 136. Flange 138 defines a flange cavity 142 and flange 140 defines a flange cavity 144. Cavities 142, 144 are configured for disposal of inner sleeve 22 such that flanges 138, 140 wrap around and slidably engage inner sleeve 22 during, for example, axial translation of the components of system 21.

Arm 116 includes projections, such as, for example, pin 146 and pin 148. Pins 146, 148 are configured for engagement with surfaces 82, 84 that are spaced apart about axial slot 86. Pins 146, 148 extend in a transverse orientation relative to a longitudinal axis within surfaces 82, 84. Pins 146, 148 engage surfaces 82, 84 such that members 98, 100 are movable between the non-expanded orientation and the expanded orientation, as described herein. It is envisioned that pins 146, 148 can be variously configured with regard to size and shape, and the shape may be rectangular, triangular, polygonal, and hexagonal, for example. It is further envisioned that the sliding contact surface may comprise a hook, clip, rod, tab, detent and/or key/keyway for slidable engagement with inner sleeve 22.

Proximal end 108 of outer sleeve 106 includes an actuator 150. Actuator 150 is configured for movable engagement with inner sleeve 22. Actuator 150 includes a first part, such as, for example, first protuberance 152 and second protuberance 154. Protuberances 152, 154 are configured for engagement with groove 30. It is envisioned that protuberances 152, 154 may be variously configured, such as those alternatives described herein.

Actuator 150 includes a knob 156. Knob 156 has a cylindrical cross-section configuration. It is contemplated that the cross-section of knob 156 may have various configurations, for example, round, oval, rectangular, polygonal, irregular, tapered, uniform and non-uniform. Knob 156 is configured for movable engagement with inner sleeve 22. Knob 156 has a faceted gripping surface. It is contemplated that the gripping surface can have alternative surface configurations, similar to those described herein. Knob 156 includes recesses 158, 160 located at an intermediate portion of knob 156. Recesses 158, 160 are round. It is envisioned that recesses 158, 160 may be alternatively configured, such as those alternatives described herein. Recesses 158, 160 are configured for fixation with protuberances 152, 154. Knob 156 includes an inner surface that defines a cavity that is configured for movable disposal of proximal end 24 of inner sleeve 22. Rotation of knob 156 causes axial translation of inner sleeve 22 relative to outer sleeve 106, as described herein.

Actuator 150 includes a pivoting member, such as, for example, tooth 162. Tooth 162 is configured for engagement with knob 156 and openings 32, 34 and 36. It is contemplated that tooth 162 may be variously configured according to the requirements of a particular application.

Tooth 162 includes a biasing member, such as, for example, button 164. Button 164 is depressible and is configured for engagement with inner sleeve 22 to bias tooth 162 into the lock openings, as described herein. Button 164 is disposed for relative movement within recess 113 and retained therein via a pin 166. Pin 166 is disposed within cavity 168 of button 164 and is fixed to openings 115, 117 of outer sleeve 106. In one embodiment, button 164 includes a spring disposed between button 164 and outer sleeve 106 within recess 113 such that tooth 162 is resiliently biased into engagement with inner sleeve 22.

Spinal implant system 21 includes a bone fastener 170. Bone fastener 170 includes a proximal portion, such as for example, a receiver 172 and a distal portion, such as for example, a shaft 174, as shown in FIGS. 17-19. Receiver 172 includes a pair of spaced apart walls defining an implant cavity. It is envisioned that the walls may have uniformly increasing or decreasing taper, arcuate, staggered and/or offset portions. In one embodiment, the inner surfaces of the walls may include internal threads. Internal threads may be configured to receive a set screw to fix the position of a vertebral rod, for example, within the implant cavity of bone fastener 170. It is envisioned that internal threads may be reverse angle threads such that threads may include a forward face that points down and in toward implant cavity. In one embodiment, the implant cavity is generally U-shaped and is configured to receive a cylindrical spinal construct, such as, for example, a vertebral rod. It is contemplated that the cross-section of the vertebral rod may have various configurations, for example, round, oval, rectangular, polygonal, irregular, tapered, offset, staggered, uniform and non-uniform. It is envisioned that the implant cavity may have other configurations, including, for example, V-shaped, polygonal, or tapered depending upon the geometry of the spinal construct to be received within the implant cavity.

The walls include a first outer surface defining a first locking cavity, such as, for example elongated locking slots and a second outer surface defining a second locking cavity, such as, for example elongated locking slots. The locking slots are configured to receive projections 74, 76 and 102, 104 respectively, for releasably locking bone fastener 170 with inner sleeve 22. It is envisioned that the locking slots may have other cross-sectional configurations, including, for example, flat bottomed channel, a cut similar to a rack and pinion, V-shaped, W-shaped, polygonal or tapered. It is further envisioned that one or both sets of the slots may be transversely oriented relative to a longitudinal axis of bone fastener 170, such as, for example, perpendicular, angled, and/or may be disposed in parallel orientation. It is contemplated that the slots allow bone fastener 170 to be captured and retained under tension and lateral compression by inner sleeve 106. It is envisioned that one or all of the surfaces of the walls have alternate surface configurations, such as, for example, rough, threaded for connection with surgical instruments, arcuate, undulating, porous, semi-porous, dimpled, polished and/or textured according to the requirements of a particular application.

It is contemplated that shaft 174 or portions thereof can have various dimensions, for example, with regard to length, width, diameter, and thickness. Shaft 174 is threaded along the length thereof and configured for penetrating tissue. Shaft 174 has a cylindrical cross section configuration and includes an outer surface having an external thread form. It is contemplated that the thread form may include a single thread turn or a plurality of discrete threads. It is further contemplated that other engaging structures may be located on shaft 174, such as, for example, a nail configuration, barbs, expanding elements, raised elements and/or spikes to facilitate engagement of shaft 174 with tissue, such as, for example, vertebrae.

It is envisioned that all or only a portion of shaft 174 may have alternate cross section configurations, such as, for example, oval, oblong, triangular, square, polygonal, irregular, uniform, non-uniform, offset, staggered, undulating, arcuate, variable and/or tapered. It is contemplated that the outer surface of shaft 174 may include one or a plurality of openings. It is further contemplated that all or only a portion of the outer surface of shaft 174 may have alternate surface configurations to enhance fixation with tissue such as, for example, rough, arcuate, undulating, mesh, porous, semi-porous, dimpled and/or textured according to the requirements of a particular application. It is envisioned that all or only a portion of shaft 174 may be disposed at various orientations, relative to the longitudinal axis of bone fastener 170, such as, for example, transverse, perpendicular and/or other angular orientations such as acute or obtuse and/or may be offset or staggered. It is further envisioned that all or only a portion of shaft 174 may be cannulated.

Figure 8:
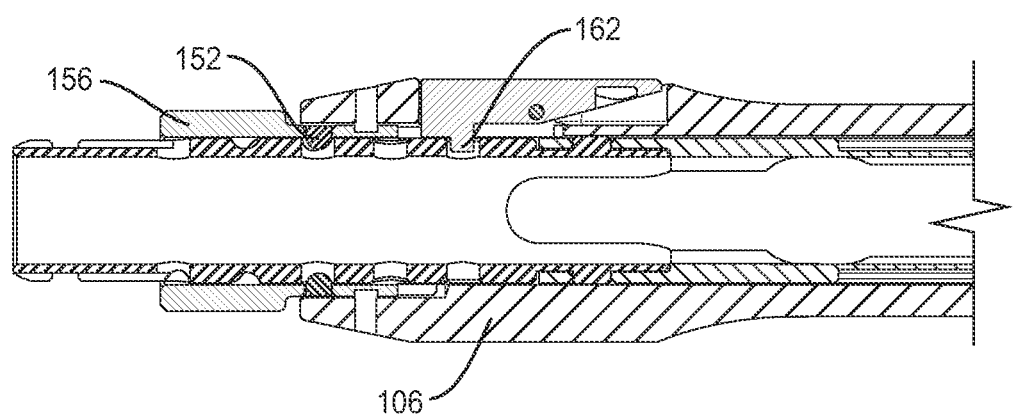
FIG. 8 is a break away cross section view of components of the system shown in FIG. 1.
Figure 9:
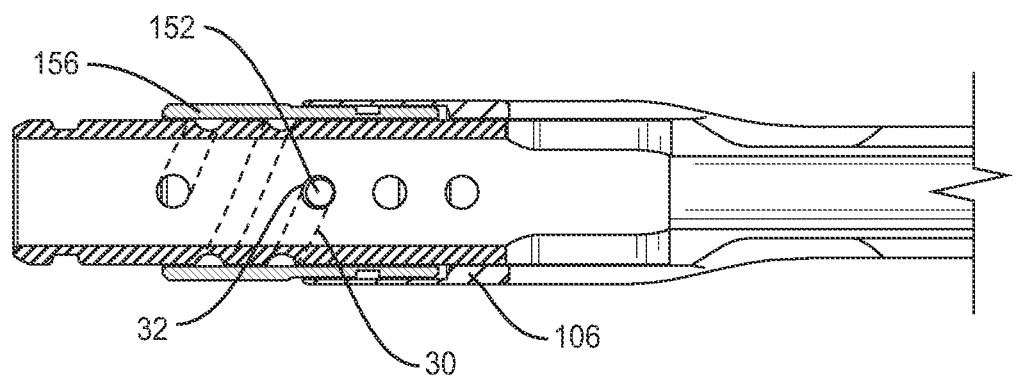
FIG. 9 is a break away cross section view of components of the system shown in FIG. 1.

In operation, the surfaces of members 70, 72 of extension 46 and members 98, 100 of extension 48 are disposed in a flush contacting engagement in the non-expanded orientation and bone fastener 170 is disposed adjacent distal end 26, as shown in FIGS. 14 and 17. Pins 130, 132 are disposed with distal portions 64, 280 of surfaces 54, 56 and pins 146, 148 are similarly disposed with distal portions 92, 286 of surfaces 82, 84. Tooth 162 is aligned with third lock opening 36 and disposed therein, as shown in FIGS. 8 and 9. Protuberance 152 is disposed adjacent first lock opening 32. Tooth 162 is releasably disposed in third lock opening 36 such that inner sleeve 22 and outer sleeve 106 are fixed in the non-expanded orientation.

To attach bone fastener 170 to inner sleeve 22 and dispose sleeves 22, 106 in a first expanded orientation, such as, for example, a load orientation, button 164 is depressed to overcome the resilient bias of button 164 and release tooth 162 from third lock opening 36. Knob 156 is rotated 180 degrees in a clockwise direction causing protuberance 152 to slidably engage groove 30. Inner sleeve 22 is freely slidable in axial translation relative to outer sleeve 22. Actuator 150 is manipulated to advance inner sleeve 22 in a distal direction relative to outer sleeve 106.

Figure 10:
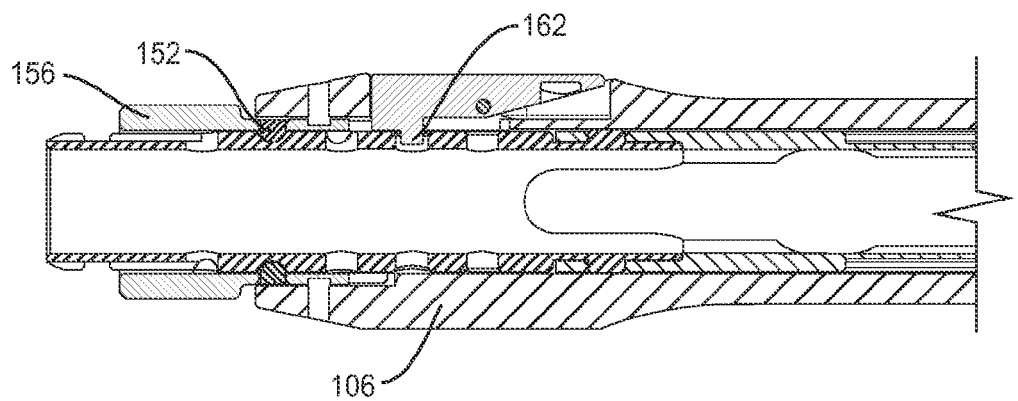
FIG. 10 is a break away cross section view of components of the system shown in FIG. 1.
Figure 11:
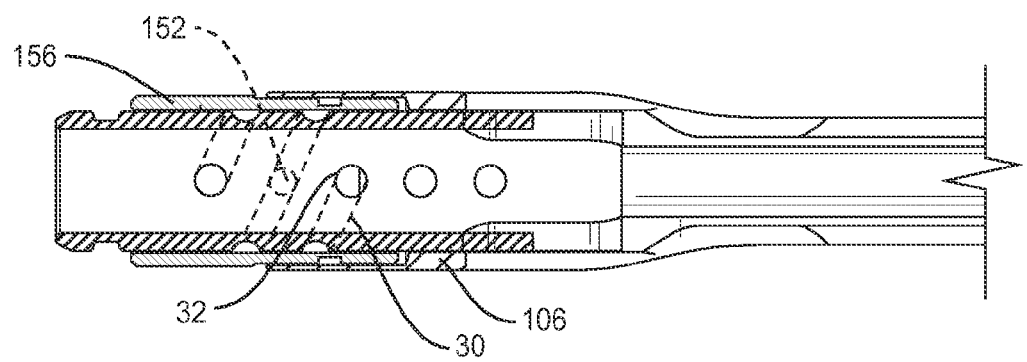
FIG. 11 is a break away cross section view of components of the system shown in FIG. 1.

Pins 130, 132 and 146, 148 axially translate in a proximal direction within surfaces 54, 56 and 82, 84 to engage ramps 66, 68 and 94, 96 and drive and space apart extensions 46, 48. Actuator 150 advances inner sleeve 22 in the distal direction relative to outer sleeve 106 such that pins 130, 132 are disposed with intermediate portions 62, 278 and pins 146, 148 are similarly disposed with intermediate portions 90, 284. Protuberance 152 is disposed with an intermediate portion of groove 30 and tooth 162 is aligned with and disposed in second lock opening 34, as shown in FIGS. 10 and 11. Tooth 162 is releasably disposed with lock opening 34 such that inner sleeve 22 and outer sleeve 106 are fixed in the load orientation. In the load orientation, extensions 46, 48 are spaced apart distance d5 adjacent distal portions 64, 280 and 92, 286; and spaced apart distance d2 adjacent proximal portions 60, 276 and 88, 282, as shown in FIGS. 15 and 18. Members 70, 72 and 98, 100 expand and separate. The lock slots of bone fastener 170 engage with projections 74, 76 and 102, 104 of members 70, 72 and 98, 100 respectively. In one embodiment, button 164 is depressed and knob 156 is rotated in a counterclockwise direction to dispose sleeves 22, 106 in a non-expanded orientation, such as, for example, a lock orientation, to lock bone fastener 170 with sleeves 22, 106.

Figure 12:
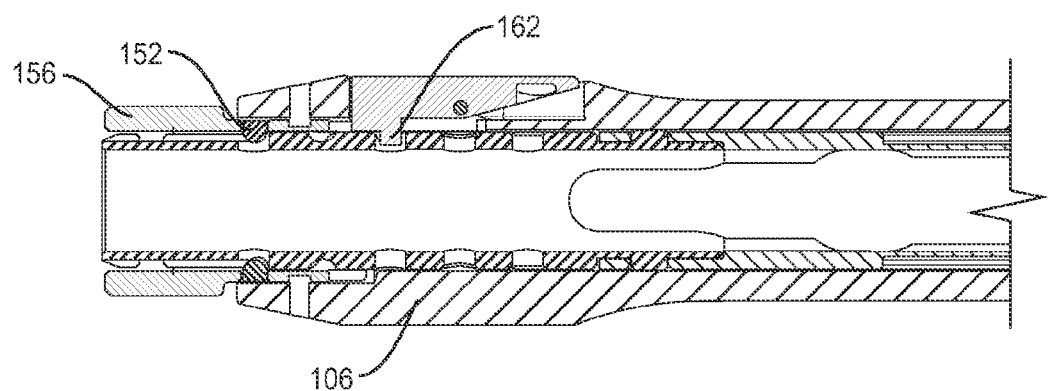
FIG. 12 is a break away cross section view of components of the system shown in FIG. 1.
Figure 13:
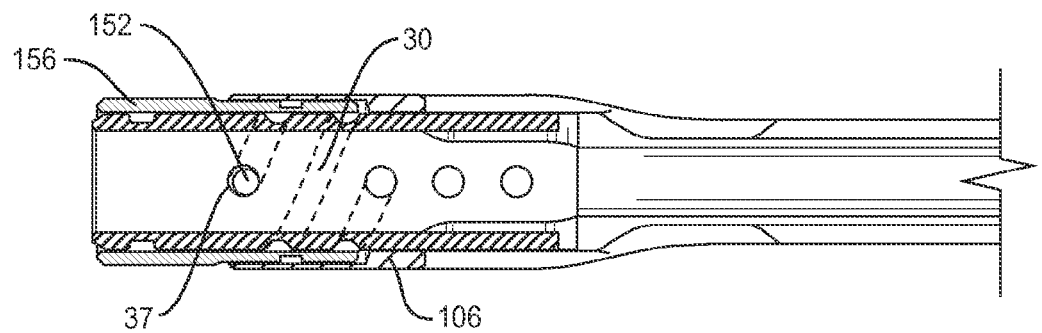
FIG. 13 is a break away cross section view of components of the system shown in FIG. 1.

To eject and/or release bone fastener 170 from inner sleeve 22 and dispose sleeves 22, 106 in a second expanded orientation, such as, for example, an eject orientation from the load orientation, button 164 is depressed to overcome the resilient bias of button 164 and release tooth 162 from second lock opening 34. Knob 156 is rotated 180 degrees in a clockwise direction causing protuberance 152 to slidably engage groove 30. Inner sleeve 22 advances in the distal direction relative to outer sleeve 106. Pins 130, 132 and 146, 148 axially translate in the proximal direction within surfaces 54, 56 and 82, 84 engaging ramps 66, 68 and 94, 96 to further space apart extensions 46, 48. Protuberance 152 is disposed adjacent opening 37 and tooth 162 is aligned with and disposed in first lock opening 32, as shown in FIGS. 12 and 13. Tooth 162 is releasably disposed with lock opening 32 such that inner sleeve 22 and outer sleeve 106 are fixed in the eject orientation. In the eject orientation, extensions 46, 48 are spaced apart distance d6 adjacent proximal portions 60, 276 and 88, 282; and spaced apart distance d3 adjacent distal portions 64, 280 and 92, 286. In the eject orientation, members 70, 72 and 98, 100 expand and separate, as shown in FIGS. 16 and 19. Projections 74, 76 and 102, 104 are manipulated to disengage from the slots of bone fastener 170 to eject bone fastener 170 from inner sleeve 22. In one embodiment, knob 156 is rotated less than 360 degrees to move and dispose sleeves 22, 106 from the non-expanded orientation to the second expanded orientation. In one embodiment, knob 156 is rotated less than 360 degrees to move and dispose sleeves 22, 106 from the second expanded orientation to the non-expanded orientation.

Figure 20:
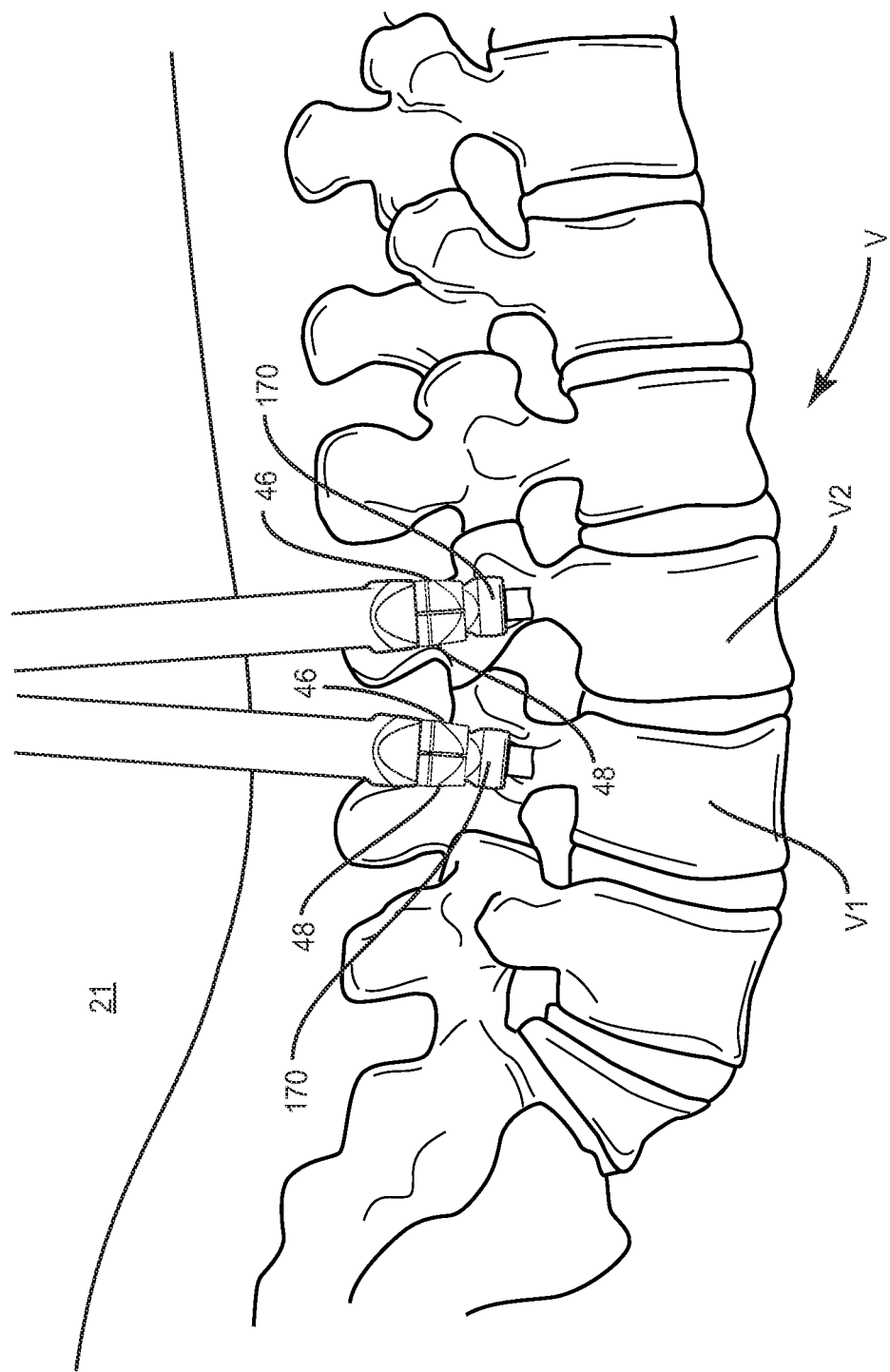
FIG. 20 is a side view of one embodiment of a system in accordance with the principles of the present disclosure disposed with vertebrae.

In assembly, operation and use, spinal implant system 21 is employed with a surgical procedure for treatment of a spinal disorder affecting a section of a spine of a patient, as discussed herein. Spinal implant system 21 may also be employed with other surgical procedures. For example, spinal implant system 21 can be used with a surgical procedure for treatment of a condition or injury of an affected section of the spine including vertebrae V, as shown in FIG. 20.

In use, to treat the affected section of vertebrae V, a medical practitioner obtains access to a surgical site including vertebrae V1, V2 in any appropriate manner, such as through incision and retraction of tissues. It is envisioned that spinal implant system 21 may be used in any existing surgical method or technique including open surgery, mini-open surgery, minimally invasive surgery, and percutaneous surgical implantation, whereby vertebrae is accessed through a micro-incision, or sleeve that provides a protected passageway to the area. Once access to the surgical site is obtained, the particular surgical procedure is performed for treating the spinal disorder. Spinal implant system 21 is then employed to augment the surgical treatment. Spinal implant system 21 can be delivered or implanted as a pre-assembled device or can be assembled in situ. Spinal implant system 21 may be completely or partially revised, removed or replaced during or after the surgical procedure.

An incision is made in the body of a patient and a cutting instrument (not shown) creates a surgical pathway for implantation of components of spinal implant system 21. A preparation instrument (not shown) can be employed to prepare tissue surfaces of vertebrae V, as well as for aspiration and irrigation of a surgical region according to the requirements of a particular surgical application. Pilot holes or the like are made in vertebrae V1, V2 for receiving the shaft of bone fastener 170. Spinal implant system 21 is disposed adjacent vertebrae V at a surgical site.

Extensions 46, 48 are disposed in a flush contacting engagement in the non-expanded orientation and bone fastener 170 is disposed adjacent distal end 26, as shown in FIGS. 14 and 17. Protuberance 152 is disposed adjacent first lock opening 32 and tooth 162 is releasably disposed in third lock opening 36, as shown in FIGS. 8 and 9, such that inner sleeve 22 and outer sleeve 106 are fixed in the non-expanded orientation.

Button 164 releases tooth 162 from third lock opening 36. Knob 156 is rotated to advance inner sleeve 22 in a distal direction relative to outer sleeve 106. Pins 130, 132 and 146, 148 drive and space apart extensions 46, 48. Protuberance 152 is disposed with an intermediate portion of groove 30 and tooth 162 is disposed in second lock opening 34, as shown in FIGS. 10 and 11, such that inner sleeve 22 and outer sleeve 106 are fixed in the load orientation. The lock slots of bone fastener 170 engage with projections 74, 76 and 102, 104 of members 70, 72 and 98, 100 respectively.

The components of spinal implant system 21 are manipulable to drive, torque, insert or otherwise connect bone fastener 170 to vertebrae and/or dispose a vertebral construct, such as, for example, a vertebral rod (not shown) with bone fastener 170, according to the particular requirements of the surgical treatment.

Button 164 is depressed to release tooth 162 from second lock opening 34 and knob 156 is rotated to advance inner sleeve 22 in the distal direction relative to outer sleeve 106. Pins 130, 132 and 146, 148 further space apart extensions 46, 48. Protuberance 152 is disposed adjacent lock opening 37 and tooth 162 is disposed in first lock opening 32, as shown in FIGS. 12 and 13, such that inner sleeve 22 and outer sleeve 106 are fixed in the eject orientation. Projections 74, 76 and 102, 104 are manipulated to disengage from the slots of bone fastener 170 to eject bone fastener 170 from inner sleeve 22.

Upon completion of the procedure, the surgical instruments and assemblies are removed and the incision is closed. Spinal implant system 21 can be made of radiolucent materials such as polymers. Radiomarkers may be included for identification under x-ray, fluoroscopy, CT or other imaging techniques. It is envisioned that the use of microsurgical and image guided technologies may be employed to access, view and repair spinal deterioration or damage, with the aid of spinal implant system 21.

It is contemplated one or a plurality of bone fasteners may be employed with a single vertebral level. It is further contemplated that the bone fasteners may be engaged with vertebrae in various orientations, such as, for example, series, parallel, offset, staggered and/or alternate vertebral levels. It is envisioned that the bone fasteners may include one or a plurality of anchors, tissue penetrating screws, conventional screws, expanding screws, wedges, anchors, buttons, clips, snaps, friction fittings, compressive fittings, expanding rivets, staples, nails, adhesives, posts, fixation plates and/or posts. These bone fasteners may be coated with an osteoinductive or osteoconductive material to enhance fixation, and/or include one or a plurality of therapeutic agents.

In one embodiment, spinal implant system 21 includes an agent, which may be disposed, packed or layered within, on or about the components and/or surfaces of spinal implant system 21. It is envisioned that the agent may include bone growth promoting material, such as, for example, bone graft to enhance fixation of the fixation elements with vertebrae V. It is contemplated that the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An extender comprising: an inner member defining a longitudinal axis and including a wall defining a thread form, the inner member further including at least one extension defining a first axial cavity and a second axial cavity, each of the axial cavities including a first portion, a second portion and a third portion, wherein the wall includes a first lock opening in communication with the thread form, a second lock opening, and a third lock opening; and an outer member including an actuator, the actuator including a protuberance, and at least one arm having a first projection disposable with the portions of the first axial cavity and a second projection disposable with the portions of the second axial cavity, the projections each extending directly from an inner surface of the at least one arm, wherein the actuator is rotatable relative to the inner member so that the protuberance engages the thread form to axially translate the inner member relative to the outer member such that the projections are disposable between a first position in which the projections are disposed with the first portions of the respective axial cavity and the inner member is disposed in a non-expanded orientation, a second position in which the projections are disposed with the second portions of the respective axial cavity and the inner member is disposed in an expanded orientation, and a third position in which the projections are disposed with the third portions of the respective axial cavity and the inner member is disposed in an expanded orientation.

2. An extender as recited in claim 1, further comprising a tooth that is pivotable relative to the outer member, wherein the lock openings are configured such that the tooth is movable into the openings to fix the inner member relative to the outer member in at least one of the positions.

3. An extender as recited in claim 2, wherein the first lock opening is configured for disposal of the tooth such that the projections are disposed in the first position, the second lock opening is configured for disposal of the tooth such that the projections are disposed in the second position and the third lock opening is configured for disposal of the tooth such that the projections are disposed in the third position.

4. An extender as recited in claim 1, wherein the first axial cavity and the second axial cavity are disposed in a parallel configuration relative to one another.

5. An extender as recited in claim 1, wherein the first portions, the second portions and the third portions are each spaced apart and disposed in parallel relation.

6. An extender as recited in claim 1, wherein the first portions are spaced apart a first dimension, the second portions are spaced apart a second dimension and the third portions are spaced apart a third dimension, the first dimension being greater than the second dimension and the second dimension being greater than the third dimension.

7. An extender as recited in claim 1, wherein the at least one extension extends to a distal end and includes a first capture member and a second capture member, wherein the capture members each include at least one fixation portion.

8. An extender as recited in claim 1, wherein the at least one extension extends to a distal end and includes a first capture member and a second capture member, the capture members being disposed in a substantially flush engagement in the non-expanded orientation and spaced apart in the expanded orientation.

9. An extender as recited in claim 1, wherein the inner member includes an inner surface that defines an implant cavity, the implant cavity defining a first dimension and a second dimension greater than the first dimension.

10. An extender as recited in claim 1, wherein the inner member includes an inner surface that defines an implant cavity that extends between a first lateral opening and a second lateral opening, the openings defining a first dimension of the inner member and a second dimension of the inner member adjacent a proximal end thereof, the second dimension being greater than the first dimension.

11. An extender as recited in claim 1, further comprising a tooth that is pivotable relative to the outer member, wherein the actuator further includes a knob having a gripping surface, the knob being rotatable relative to the at least one arm of the outer member.

12. An extender as recited in claim 1, further comprising a second protuberance.

13. An extender as recited in claim 1, wherein the actuator is rotated relative to the inner member to a selected angular orientation to dispose the projections in the second position from the first position and in the third position from the second position.

14. An extender as recited in claim 1, wherein the actuator comprises a tooth that is pivotable relative to the outer member, wherein the actuator is coupled to the outer member and the tooth is engageable with the inner member to releasably fix the projections separately in the first position, the second position and the third position.

15. An extender as recited in claim 14, wherein the tooth includes a biasing member configured for engagement with the inner member to bias the tooth into the lock openings of the wall corresponding to the positions.

16. An extender as recited in claim 1, wherein the at least one arm includes at least one flange that defines a flange cavity configured for disposal of a distal end of the inner member.

17. An extender as recited in claim 1, wherein the projections are spaced apart from one another and are monolithically formed with the inner surface of the at least one arm.

18. An extender as recited in claim 1, wherein the thread form is a helical groove and the inner member comprises an aperture configured to provide visual inspection of an interior cavity of the inner member, the aperture and the first lock opening extending through the helical groove such that the aperture defines a first end of the helical groove and the first lock opening defines a second end of the helical groove.

19. An extender comprising:
an inner sleeve extending between a proximal end and a distal end, the inner sleeve including a longitudinal axis and a wall defining openings and a helical groove, the openings including a first lock opening in communication with the helical groove, a second lock opening and a third lock opening, the inner sleeve further including a first extension and a second extension, each extension defining a first axial cavity and a second axial cavity, each of the axial cavities including a first portion having a first dimension, a second portion having a second dimension and a third portion having a third dimension, the first dimension being greater than the second dimension and the second dimension being greater than the third dimension, each portion being spaced apart and disposed in parallel relation, a distal end of each extension including capture members that include at least one fixation portion, the inner sleeve further including an inner surface that defines an implant cavity, the implant cavity extending between a first lateral opening and a second lateral opening, the lateral openings defining a first dimension of the inner sleeve and a second dimension adjacent a proximal end thereof, the second dimension being greater than the first dimension; and
an outer sleeve including a knob having a gripping surface and including a first protuberance and a second protuberance, the outer sleeve further including a first arm and a second arm, each arm having at least one inward projection disposed for movement within each of the first axial cavities and second axial cavities, the inward projections each extending directly from an inner surface of one of the arms, each arm having flanges that define flange cavities configured for engagement with a distal end of the inner sleeve during axial translation of the inner sleeve member relative to the outer sleeve, wherein the knob is rotatable relative to the inner sleeve to a selected angular orientation such that the first and second protuberances engage the helical groove to axially translate the inner sleeve relative to the outer sleeve such that the projections are disposable between a first position such that the projections are disposed with the first portions of the respective axial cavity and the inner sleeve is disposed in a non-expanded orientation, a second position such that the projections are disposed with the second portions of the respective axial cavity and the inner sleeve is disposed in a first expanded orientation, and a third position such that the projections are disposed with the third portions of the respective axial cavity and the inner sleeve is disposed in a second expanded orientation.

20. A spinal implant system comprising:

an extender comprising an inner sleeve extending between a proximal end and a distal end and defining a longitudinal axis and an outer sleeve extending between a proximal end and a distal end, the inner sleeve including a wall defining a thread form and lock openings, the lock openings including a first lock opening in communication with the thread form, a second lock opening and a third lock opening, the inner sleeve further including a first extension and a second extension, each extension defining a first axial cavity and a second axial cavity, each of the axial cavities including a first portion having a first dimension, a second portion having a second dimension and a third portion having a third dimension, the first dimension being greater than the second dimension and the second dimension being greater than the third dimension, distal ends of the extensions including a first capture member and a second capture member, each capture member having at least one fixation portion, the outer sleeve including an actuator including a first protuberance and a second protuberance, the outer sleeve further including a first arm and a second arm, each arm having a first inward projection disposed for movement within the first axial cavity and a second inward projection disposed for movement within the second axial cavity, the projections each extending directly from an inner surface of the arms, the arms further including flanges that define flange cavities configured for disposal of the extensions such that the flanges slidably engage the extensions during axial translation, and a bone fastener including a proximal portion that defines an implant cavity and a distal portion configured to penetrate tissue, wherein the actuator is rotatable relative to the inner sleeve and the protuberances engage the thread form adjacent the first lock opening such that the projections are disposed with the first portions of the respective axial cavity and the inner sleeve is disposed in a non-expanded locking orientation, and rotation of the actuator moves the protuberances to a second position such that the projections are disposed with the second portions of the respective axial cavity and the inner sleeve is disposed in a first expanded loading orientation, and further rotation of the actuator moves the protuberances to a third position such that the projections are disposed with the third portions of the respective axial cavity and the inner sleeve is disposed in a second expanded eject orientation.

* * * * *

UNITED STATES PATENT AND TRADEMARK OFFICE
CERTIFICATE OF CORRECTION

PATENT NO. : 9,451,998 B2
APPLICATION NO. : 13/588765
DATED : September 27, 2016
INVENTOR(S) : McBride et al.

Page 1 of 1

It is certified that error appears in the above-identified patent and that said Letters Patent is hereby corrected as shown below:

In the specification

In Column 13, Lines 32-33, delete "inner sleeve 106." and insert -- inner sleeve 22. --, therefor.

Signed and Sealed this
Twentieth Day of December, 2016

Michelle K. Lee
*Director of the United States Patent and Trademark Office*